United States Patent [19]
Reffner et al.

[11] Patent Number: 5,616,922
[45] Date of Patent: Apr. 1, 1997

[54] OPTICALLY COUPLED INFRARED TRANSMITTING COMPOSITE INTERNAL REFLECTING ELEMENTS

[76] Inventors: John A. Reffner, 97 Ocean Dr., East, Stamford, Conn. 06902; Milan Milosevic, 10 Alden Ct., Fishkill, N.Y. 12524; Donald W. Sting, 358 Turtleback Rd., New Canaan, Conn. 06840

[21] Appl. No.: 500,552

[22] Filed: Jul. 11, 1995

Related U.S. Application Data

[63] Continuation-in-part of Ser. No. 28,388, Mar. 9, 1993, abandoned.

[51] Int. Cl.$^6$ ................................................ G01N 21/35
[52] U.S. Cl. ........................ 250/339.12; 250/339.11; 250/341.8
[58] Field of Search .................. 250/339.12, 343, 250/339.11, 341.8, 339.07; 359/350

[56] References Cited

U.S. PATENT DOCUMENTS

| | | |
|---|---|---|
| 4,595,833 | 6/1986 | Sting . |
| 4,730,882 | 3/1988 | Messerschmidt . |
| 5,007,689 | 4/1991 | Kelly et al. .................... 359/350 |
| 5,067,781 | 11/1991 | Montanari et al. .............. 359/350 |
| 5,120,602 | 6/1992 | Tustison et al. ............. 359/350 X |
| 5,172,182 | 12/1992 | Sting et al. . |
| 5,225,926 | 7/1993 | Cuomo et al. ................... 359/350 |
| 5,434,411 | 7/1995 | Miyahara et al. .......... 250/339.12 X |

FOREIGN PATENT DOCUMENTS

| | | | |
|---|---|---|---|
| 59-176701 | 10/1984 | Japan | ................ 359/350 |
| 64-9401 | 1/1989 | Japan | ................ 359/350 |
| 64-56401 | 3/1989 | Japan | ................ 359/350 |
| 5-150101 | 6/1993 | Japan | ................ 359/350 |

OTHER PUBLICATIONS

"Spectroscopy with the Evanescent Wave in the Visible Region of the Spectrum," Gerhard J. Müller, 1979, American Chemical Society pp. 239–262.

"Optical materials for Infrared Instrumentation," Stanley S. Ballard, Kathryn A. McCarthy and William L. Wolfe, 1959, pp. 38–47.

"Internal Reflection Spectroscopy: Review and Supplement," Francis M. Mirabella Jr. and N. J. Harrick, Editor, 1985, pp. 98–99.

*Primary Examiner*—Edward J. Glick

[57] ABSTRACT

An apparatus and method for spectroscopic or radiometric analysis of solid, liquid, or gas samples includes first and second optically transmitting materials. The first optically transmitting material has selected bulk optical transmission and index of refraction properties which enable infrared radiation transmission therethrough across selected optical transmission ranges. The first optically transmitting material is of a type which normally has chemical or mechanical degradation when in contact with the sample during spectroscopic or radiometric analysis. The second optically transmitting material is preferably a wafer or thin sheet in optical/mechanical contact with the first optically transmitting material. The second material is designed to be located between the first optically transmitting material and the sample all held in a fixture or fixtures to prevent the sample from contacting the first material during spectroscopic or radiometric analysis of the sample. The second optically transmitting material: i) is chemically resistant to the sample, ii) is constructed of a material which prevents significant physical degradation of the second material when the sample contacts the second material, iii) has selected optical transmission and index of refraction properties which enable optical transmission from the first material to the second material, or from the second material to the first material, without significant transmission or reflectivity losses, and iv) is contained in a cell or fixture that prevents the sample from contacting the first optically transmitting material during the spectroscopic or radiometric analysis.

17 Claims, 4 Drawing Sheets

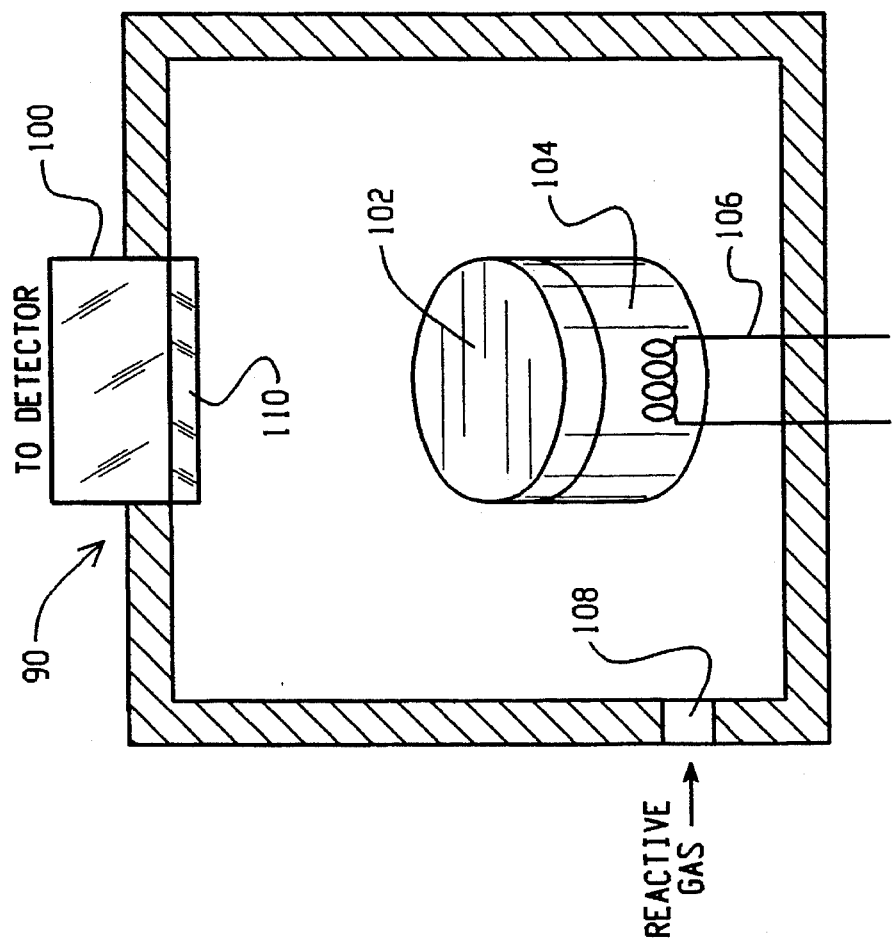
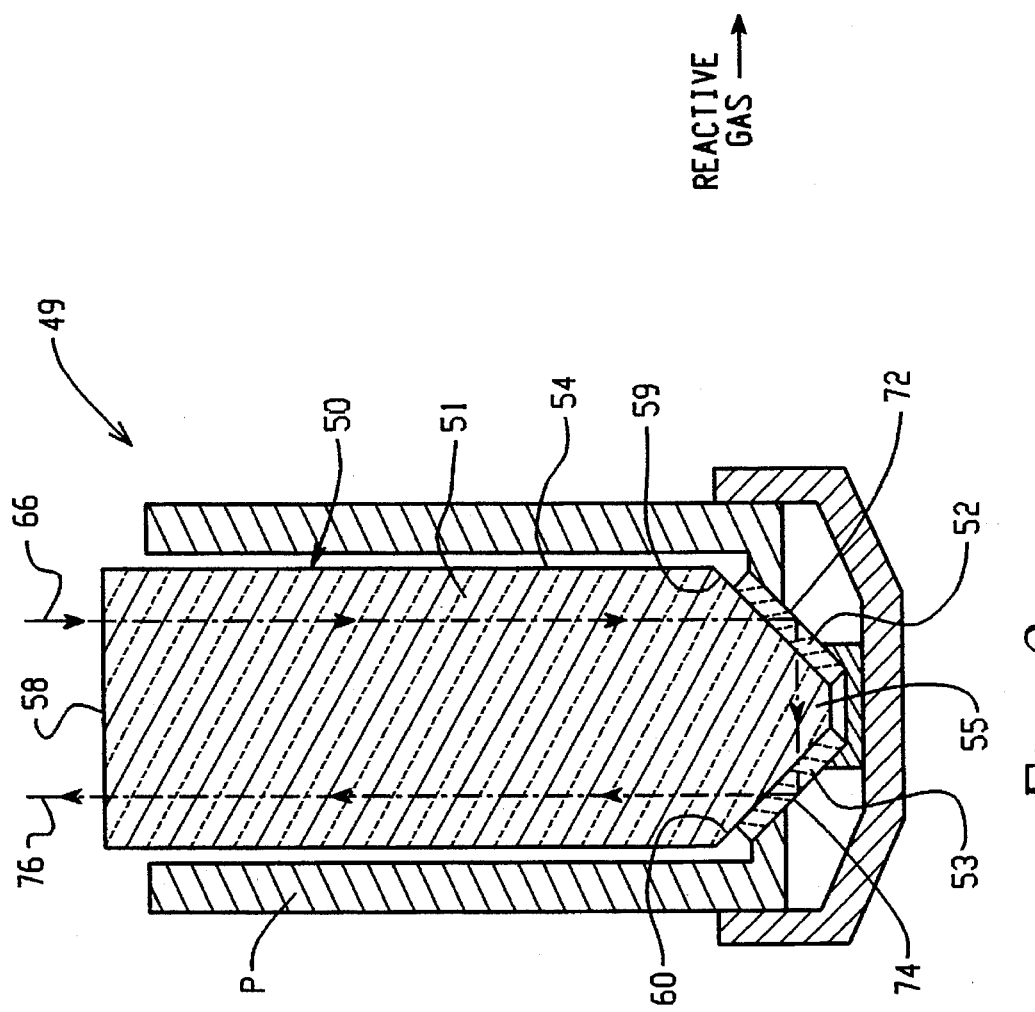
Fig. 3
Fig. 2

OPTICALLY COUPLED INFRARED TRANSMITTING COMPOSITE INTERNAL REFLECTING ELEMENTS

RELATED APPLICATIONS

This application is a continuation-in-part of U.S. application Ser. No. 08/028,388, filed Mar. 9, 1993, abandoned.

FIELD OF THE INVENTION

The present invention relates generally to composite infrared transmitting materials (ITMs) used to contain or contact a sample for spectroscopic analysis, and more particularly, to composite internal reflecting elements (IRE's), composite transmission cells and composite emission cells for infrared spectroscopic analysis of a sample.

BACKGROUND OF THE INVENTION

Infrared spectroscopy (and radiometry) has been accepted as an analytical technique for the analysis of solids, liquids and gasses. In general, infrared-absorption spectroscopic analysis of a sample involves a source of infrared (IR) analytical radiation, a detector or analyzer, and optical transmitting means for directing the analytical radiation from the source to the sample (which reflects and absorbs portions of the radiation), and for directing reflected or unabsorbed portions of the radiation from the sample to the detector. Alternatively, infrared-emission spectroscopic analysis uses the sample itself as a source of analytical radiation. By analyzing the returning or emitted beam of radiation in these techniques, and in particular the absorption pattern of the beam, certain absorption (or emission) characteristics of the sample can be determined.

In order to perform infrared spectroscopic analysis, it is usually necessary to use ITMs to contain or bound the sample (when performing transmission and/or emission experiments), or to contact the sample (when performing internal-reflection spectroscopic experiments). Since an ITM is typically in physical contact with the sample, the optical properties of the ITM affect the radiation received by the detector. When an ITM does not transmit energy of specific wavelength regions, the ITM is said to be opaque in that region. When used to contain, bound, or contact a sample for spectroscopic analysis, spectroscopic information about the sample cannot be obtained in the opaque spectral region. In order to obtain spectroscopic information when using an ITM, the ITM must transmit sufficient radiant energy through the specific wavelength regions to allow radiant energy from the source to reach the sample and transmit that radiant energy (after encoding with the sample's absorption information) so that it reaches the detector.

Since many ITMs are in physical contact with the sample, an ITM must be chemically inert to the sample under the pressure, temperature, and flow conditions imposed on both the sample and the ITM during analysis. For example, the ITM must resist abrasion, scratching, corrosion and stress from the sample during analysis. In addition, the surface properties and qualities of an ITM are important. If a sample interacts with an ITM, the sample may form unacceptable precipitates or thin films on the ITM's surface.

Different ITMs have different chemical and mechanical properties. Typically, it is necessary to match the chemical and mechanical properties of the ITM to those of the sample or class of samples being analyzed. However, it is believed that there is no one material that exhibits all of the desirable qualities for an ITM. For example, zinc selenide (ZnSe) is a widely-used ITM for internal-reflection spectroscopy (IRS). It has relatively broad optical-transmission properties [20,000–500 $cm^{-1}$ (0.5–20 µm)], has a desirable refractive index for IRS [2.40 at 1,100 $cm^{-1}$], and is modest in cost when used in analytical laboratories with a large number of routinely-used solvents and products. In addition, it has an acceptable lifespan when treated with care using standard laboratory practices.

Unfortunately, ZnSe is soft when compared to materials such as laboratory glassware, is easily abraded when placed in contact with harder materials, and is easily degraded when subjected to most solvents under elevated temperatures and pressures or to strong acids or bases.

Another widely-used ITM is KRS-5 (TlBr-TlI). Again, this ITM exhibits highly-desirable optical properties, but is very soft and easily damaged or degraded with normal use.

On the other hand, diamond is a material with highly-desirable mechanical properties and chemical resistivity. However, diamond is relatively expensive and is available in only limited sizes and shapes (except at very high costs).

Other materials used for ITMs include Amtir (glass), arsenic-modified selenium glass (SeAs), cadmium sulfide (CdS), cadmium telluride (CdTe), cesium iodide (CsI), diamond (C), germanium (Ge), indium antimonide (InSb), silicon (Si), sapphire ($Al_2O_3$), silver bromide (AgBr), silver chloride (AgCl), sulfur (S), sulfur-selenium glasses ($S_xSe_y$), thallium bromide (TlBr), thallium chloride (TlCl), zinc sulfide (ZnS), zirconia ($ZrO_2$, cubic), sodium chloride (NaCl), potassium bromide (KBr), and potassium chloride (KCl), among others. However, there is no known ITM with all of the qualities required for a wide range of uses at acceptable costs.

Diamond-like coatings (DLCs) have been deposited on materials such as ZnSe or ZnS to provide an ITM window. However, it is believed that the current state of the art (as known to the inventors) is inadequate to provide commercially-acceptable and economical composite ITMs, and in particular, it is believed that DLCs cannot withstand the chemical and mechanical attacks normally required of ITMs, and are prone to crazing or peeling in some situations. These problems appear to be largely due to the differences in the mechanical properties of the coefficient of thermal expansion of the two or more materials bonded together in the composite and to the imperfections of the coatings of the materials.

Over the years, attempts have been made to develop new composite ITMs by using chemical-vapor deposition or other techniques to bond two or more materials together. While it is believed that a certain amount of success has been achieved in the development of some composite ITMs, there is no widely-acceptable composite ITM available to date.

The deposition of a sample on the surface of windows or internal reflection elements (IRE) is a related problem where composite ITMs could be used. Removal of deposits often requires aggressive mechanical or chemical cleaning that can damage the ITM. Using a removable and disposable plate of the same material as the IRE was a solution to this problem proposed by Gerhard J. Muller, "Spectroscopy with the Evanescent Wave in the Visible Region of the Spectrum", Multichannel Image Detectors, American Chemical Society, 1979 (hereinafter "Muller"). This prior art teaches the use of liquids to optically couple two solid optical elements of the same material to form a temporary composite internal reflection spectral analysis unit for use with visible light. Using liquids to achieve optical contact is a common practice for visible radiation, since transparent liquids are readily available in this spectral range. However, in the infrared spectral region transparent liquids are not available. Muller does not teach or suggest any method or means for optically coupling ITMs in the infrared spectral region. To the inventors' knowledge, bromine and carbon diselenide are the only liquids that would be transparent in the mid-infrared spectral region. Sulfur-selenium mixtures melt below 150° C. and form glasses on cooling. These melts are transparent in the mid-infrared, but the glasses crystallize and are not reliable as optical coupling materials. Diamond is an ITM that can withstand aggressive cleaning, but large, thick diamond windows or IREs are very expensive and therefore impractical for most applications.

Hence, until now, there have been certain drawbacks in providing an ITM which simultaneously has a broad (or selected) optical transmission range; chemical resistivity to the sample; appropriate mechanical strength; and acceptably low cost, for use in spectroscopic (or radiometric) analysis.

SUMMARY OF THE INVENTION

The present invention provides novel and unique composite infrared transmitting materials (ITMs) used to contain or contact a sample for spectroscopic (or radiometric) analysis, and in particular, composite IREs, composite transmission cells, and composite emission cells. The composite infrared transmitting materials have a broad (or selected) optical transmission range, chemical resistivity to the sample, appropriate mechanical strength, and relatively low cost. These composite ITMs are held in optical/mechanical contact without a fixed adhesive, chemical or mechanical bond between the transmitting surfaces of the ITMs.

The composite ITMs of the present invention include first and second optically transmitting materials (OTM). In forming the composite ITMs for spectroscopic analysis, optical contact is provided between the first and second optically transmitting materials. By optically contacting the first and second materials, minimal energy loss occurs across the material interface. A mechanical cell or fixture maintains optical contact between the ITMs and prevents the sample from coming in contact with the first OTM.

The term "optical contact" refers to the fact that the physical separation between the two infrared-transmitting materials (ITMs) is so small that the optical properties of the interface are determined solely by the difference in optical properties between the two ITMs. Although there is no fixed chemical or adhesive bond between these two materials, the optical properties of the interface are determined solely by the difference in optical properties between the two materials. For example, the reflectivity of the interface would be determined by the ratio of the square of the difference divided by the sum of the two refractive indices. The space between the ITMs does not contribute to the optical properties of the interface. Optical contact is especially important in composite internal-reflection elements (IREs). If optical contact is not made between the various components in the laminate IREs, then total internal reflection would occur at these interfaces. With optical contact, the radiant energy will pass through the interface with little loss.

Because there is no fixed chemical, adhesive, or physical bond between the transmitting surfaces of the elements of the composite ITMs of this invention, the components of a laminate can move independently. This is most important when composite ITMs are subjected to temperature changes, wherein differences in thermal expansion coefficients cause the components to expand and contract to different extents. If chemical, adhesive, or mechanical bonding occurs at the interface, then mechanical stress develops at the interface during thermal cycles, causing failures of bonded composite ITMs. The present invention provides methods and means for allowing critical freedom of movement at the interface of the ITM materials without mechanical or chemical breakdown, or optical distortion. For example, the thermal-expansion coefficient for zinc selenide is $7.1 \times 10^{-6}$, while that of diamond is $0.8 \times 10^{-6}$. Hence, zinc selenide expands 8.9 times more than diamond. In the prior art, diamond has been used as a protective layer between a sample and an IRE such as zinc selenide. However, when diamond is bonded to zinc selenide, the bond between the two materials and the material coatings fail when exposed to thermal cycles because of differences in coefficients of thermal-expansion of the adjacent materials. The present invention overcomes this problem by providing optical contact by mechanical coupling between an IRE and a sample-protective layer using materials with suitable optical, chemical and mechanical properties. By maintaining the structural integrity of each component of this laminate and the bonds between the materials, the invention provides laminated ITMs that can withstand thermal cycling.

According to one embodiment of the present invention, the composite ITM comprises a composite internal reflecting element (IRE). Preferably, the composite IRE is a multi or single-bounce IRE, or a multi or single-bounce attenuated total reflecting (ATR) element. The composite IRE includes an IRE having selected bulk optical transmission and index of refraction properties which enable infrared radiation transmission therethrough across selected optical transmission ranges. The IRE also has an acceptably low cost. However, the IRE is of a type which normally has chemical or mechanical degradation when in contact with the sample during spectroscopic (or radiometric) analysis.

The second optically transmitting material for the composite IRE is located between the IRE and the sample to prevent the sample from coming in contact with the first material during spectroscopic or radiometric analysis. The second OTM is held in optical contact with the IRE by a mechanical structure which also prevents the sample from contacting the first OTM. The second optically transmitting material: i) is substantially chemically resistant to the sample, ii) has mechanical properties which prevent significant physical degradation of the second material when the sample contacts the second material during spectroscopic or radiometric analysis, iii) has selected optical transmission and index of refraction properties which enable optical transmission from the first material to the second material, or from the second material to the first material under various environmental conditions without substantial transmission or reflectivity loss, and iv) is held in a cell or fixture which prevents the sample from contacting the IRE. Preferably, the second optically transmitting material is a wafer or thin sheet which is in optical contact with the IRE.

According to other embodiments of the present invention, the composite ITM comprises a composite emission cell or a composite transmission cell. The composite emission cell and the composite transmission cell also include IR transmitting material with selected bulk optical transmission and index of refraction properties which enable infrared radiation transmission therethrough across selected optical transmission ranges. The IR transmitting material of the composite transmission and emission cells is also of a relatively low cost. However, the transmitting material is also of a type which normally has chemical or mechanical degradation when in contact with the sample during spectroscopic (or radiometric) analysis.

According to these and other embodiments, the second optically transmitting material for the composite transmission cell and the composite emission cell is also designed to be located between the IR transmitting material and the sample to prevent the sample from contacting the IR transmitting material during spectroscopic or radiometric analysis. The second optically transmitting material: i) is substantially chemically resistant to the sample, ii) has mechanical properties which prevent significant physical degradation of the second material when the sample contacts the second material during spectroscopic or radiometric analysis, iii) has selected optical transmission and index of refraction properties which enable optical transmission from the IR transmitting material to the second material, or from the second material to the IR transmitting material, without substantial transmission or reflectivity loss, and iv) is contained or held in a cell or fixture that prevents the sample from contacting the IRE. Preferably, the second optically transmitting material is a wafer or thin sheet which is located in optical contact with the IR transmitting material.

The composite ITM of any of the embodiments described above can be incorporated into a spectroscopic or radiometric instrument. The instrument has a source of analytical radiation which is directed by the composite ITM to the sample. The instrument also includes a detector or analyzer which receives the analytical radiation from the sample for determining the sample's absorption characteristics. Alternatively, for emission experiments, the detector or analyzer receives the radiation directly from the sample.

It is therefore an object of the present invention to provide a composite ITM which has a broad (or selected) optical transmission range, chemical resistivity to the sample, appropriate mechanical strength, able to operate over a large temperature range, and relatively low cost.

These and other objects of the present invention are apparent from the following detailed description of the preferred embodiments made with reference to the accompanying drawings.

BRIEF DESCRIPTION OF THE DRAWINGS

FIG. 2 is similar to FIG. 1, but showing another exemplary type of multi-bounce composite IRE constructed according to the present invention;

FIG. 3 is an exemplary type of composite emission cell constructed according to the present invention having an IR transmitting thin sheet or wafer shown in contact with the sample.

DETAILED DESCRIPTION OF THE PREFERRED EMBODIMENT

Figure 1:
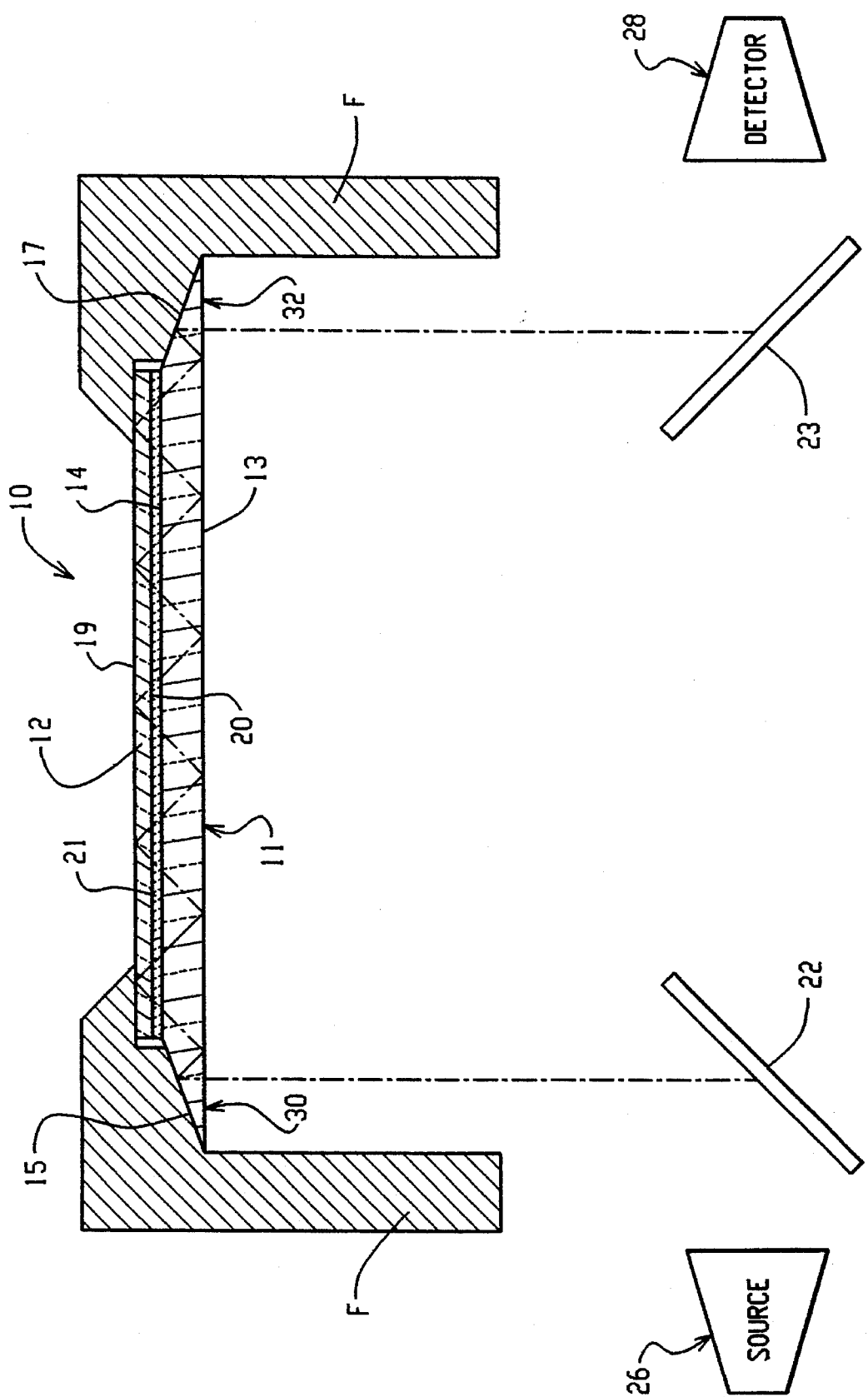
FIG. 1 is an elevation of one exemplary type of multi-bounce composite internal reflectance element constructed according to the present invention having an IR transmitting wafer or thin sheet shown in contact with a sample.

Referring to the drawings and initially to FIG. 1, one type of composite infrared transmitting material (ITM) is indicated generally at 10. According to one embodiment of the present invention, the composite ITM comprises a composite internal reflecting element (IRE). The composite IRE includes an IRE, generally referred to at 11, and an IR transmitting thin wafer or sheet 12 (hereinafter referred to simply as a "wafer"). The wafer 12 is held in relation to IRE 11 by a fixture F to protect the IRE from chemical and mechanical degradation. As such, the composite ITM can be formed from materials which have relatively lower costs, thus reducing the overall cost of the spectroscopic or radiometric instrument.

The IRE 11 preferably has a lower surface 13; an upper surface 14; and first and second bevelled edges 15, 17. The lower and upper surfaces 13, 14, of the IRE can be optically flat, or can have some other geometry, such as spherical, aspherical or cylindrical. The IRE 11 illustrated in FIG. 1 is generally referred to as a multi-bounce Attenuated Total Reflection (ATR) element. Such an IRE is described in detail in Messerschmidt, U.S. Pat. No. 4,730,882. A similar IRE having a cylindrical shape is disclosed in Sting, U.S. Pat. No. 4,595,833. Either IRE geometry disclosed in these references is appropriate for the present invention. Both of these references also disclose other components of spectroscopic instruments with which the IREs are used.

The composite IRE can be formed from any of the optically transmitting materials which are known in the art for IRE's. For example, the IRE can be formed from Amtir (glass), arsenic-modified selenium glass (SeAs), cadmium sulfide (CdS), cadmium telluride (CdTe), cesium iodide (CsI), germanium (Ge), indium antimonide (InSb), KRS-5 (TlBr-TlI), silicon (Si), silver bromide (AgBr), silver chloride (AgCl), sulfur (S), sulfur-selenium glasses ($S_xSe_y$), thallium bromide (TlBr), thallium chloride (TlCl), zinc selenide (ZnSe), zinc sulfide (ZnS), and zirconia ($ZrO_2$, cubic), among others.

The present invention is not limited to any particular IRE geometry or material, but rather applies to the whole range of known IRE geometries and materials for spectroscopic and radiometric analysis. In fact, as will be described herein, the present invention also applies to other types of infrared transmission materials for sample contact or containment, such as emission cells and transmission cells, or to any other type of ITM which is used for analytical purposes.

In any case, the materials described above have broad or selected optical transmission properties and appropriate index of refraction properties which make the materials desirable for spectroscopic or radiometric analysis, i.e., the level of IR transmission through these materials is acceptable for detailed spectroscopic or radiometric analysis. However, these materials nonetheless have relatively poor chemical and mechanical resistivity to some sample materials.

To prevent degradation (both mechanical and chemical) of IRE 11 when in contact with a sample during spectroscopic or radiometric analysis, the wafer 12 is held by fixture F between the sample and the IRE 11 to provide an optically transparent physical barrier between IRE 11 and a sample. A less expensive material can thus be used for the IRE with little or no reduction in optical transmission properties, which thereby reduces the overall cost of the spectroscopic or radiometric system. The wafer 12 typically covers the entire exposed surface area of the IRE 11; however, it is possible that the wafer only covers as much of the upper surface area of the IRE as will potentially come into physical contact with the sample, which is typically slightly less than the entire upper surface of the IRE. Hence, when the sample is introduced into contact with the composite IRE, the wafer 12 held by mounting fixture F acts as a physical barrier between the sample and the IRE 11.

The wafer 12 for the composite IRE preferably has an upper surface 19, and a lower surface 20. The upper and lower surfaces 19, 20 can be optically flat, or one (or both) of these surfaces could be curved (e.g., concave), depending on the geometry of the underlying IRE. The lower surface 20 of the wafer 12 is located in opposing planar parallel relation to the upper surface 14 of the IRE 11. More particularly, the wafer is located as close as possible to the IRE such that "optical coupling" occurs between the wafer and the IRE (i.e., optical transmission occurs across the interface between the two materials with minimal reflectivity or transmission losses). Optical coupling can be achieved without direct physical contact of two surfaces. By appropriate adjustment of fixture F, preferably the wafer is located less than 2 microns away from the IRE; however, the distance can be varied depending upon the wavelength of the radiation beam and the acceptable transmission/reflectivity losses during analysis, as should be known to those skilled in the art.

Such optical coupling can be accomplished by close tolerance arrangement of "optically correct" surfaces, for example by relative positioning within a fixture F; or by optical coupling of mated surfaces (without direct physical contact of the two surfaces) with an optically compatible, easily deformable plastic/elastic solid or gel, having a viscosity generally greater than liquid. Herein, an "optically correct" surface is defined as being a shape(s) which is no more than 1 micron from a theoretically correct shape (e.g., flat, spherical or aspheric).

Further, a relatively thin deformable solid or gel-type (non-liquid) intermediate layer 21 of optically transmitting material can be interposed between the IRE 11 and the wafer 12. Layer 21 achieves optically coupling between wafer 12 and IRE 11 with optical transmission and refractive index properties such that there is minimal optical transmission and reflectivity losses between IRE 11 and wafer 12. In general, using a third optically transmitting layer between the IRE and the wafer compensates for any surface irregularities in the IRE and wafer and allows the surface tolerances to be somewhat relaxed. This technique eliminates the expensive necessity in the prior art to highly polish mating surfaces which are to be optically coupled. Preferred material for intermediate layer 21 includes KRS-5, Thallium Bromide, Cesium Iodide, Sulfur, Selinium, Thallium Iodide, Silver Chloride, and Silver Bromide.

Optically coupling wafer 12 to IRE 11 by use of a deformable but non-liquid intermediate layer 21 having plastic/elastic properties allows the wafer to translate or displace relative to IRE 11, and hence allows for expansion, contraction, stress, shock, etc. of the composite IRE during spectroscopic or radiometric analysis of the sample without damaging the wafer, the IRE or the sample.

The wafer 12 is preferably formed (e.g., ground and highly polished) from a material which has transmission and index of refraction properties which are compatible (i.e., similar) to the optical transmission and index of refraction properties of the underlying IRE. When the wafer and the IRE are optically coupled together (with or without an intermediate layer), minimal transmission or reflectivity losses occur across the material interface. In general, the reflectivity of the interface increases by the square of the differences in the refractive indices divided by the sum of the refractive indices in non-absorbing spectral regions ($R=((n_1-n_2)/(n_1+n_2))^2$). The choice of wafer and IRE material can be easily determined by those of ordinary skill in the art knowing the appropriate index of refraction and optical transmission properties of the materials.

Moreover, according to the principles of the present invention, the wafer is also formed from a material which is substantially chemically and mechanically resistant to the sample. For example, if the sample is water, the wafer is formed from a material which is chemically and mechanically resistant (e.g., inert) to water. Such materials appropriate for the wafer 12 include: Amtir (glass), arsenic-modified selenium glass (SeAs), barium titanite ($BaTiO_3$), cadmium sulfide (CdS), cadmium telluride (CdTe), diamond (C), germanium (Ge), indium antimonide (InSb), sapphire ($Al_2O_3$), silicon (Si), silver bromide (AgBr), silver chloride (AgCl), strontium titanate ($SrTiO_3$), sulfur (S), thallium bromide (TlBr), thallium chloride (TlCl), titanium dioxide ($TiO_2$), zinc selenide (ZnSe), zinc sulfide (ZnS), and zirconia ($ZrO_2$, cubic), among others. However, as should be appreciated by those skilled in the art, other materials than those described above are also appropriate for the wafer as long as the wafer material has the above-mentioned optical transmission, index of refraction, and chemical and physical properties.

The thickness of the wafer 12 will vary depending on the material used for the wafer and the particular sample being analyzed. However, in general, the wafer should be thick enough to provide sufficient chemical and mechanical resistance when in contact with the sample, such as being resistant to abrasion, pressure, temperature changes, and cracking. On the other hand, the wafer 12 should be thin enough so as to minimize absorption and cost. In general, absorption depends upon the absorptivity of the material (at a selected wavelength), multiplied by the thickness of the material, and multiplied by the concentration of the material. Accordingly, by minimizing the thickness of the wafer, the absorption by the wafer material will likewise be minimized.

In light of the above factors, it has been determined that the wafer should generally have a thickness of between about 100 microns and 1 millimeter for most of the wafer materials identified above. However, for certain high pressure applications, 2 or 3 millimeters of wafer material may be required.

As an example, for an IRE formed from Cesium Iodide, a wafer can be used which is formed from Sapphire to spectroscopically analyze water. Such a wafer should preferably have a thickness of about 100 microns to prevent chemical and mechanical degradation of the composite IRE. As should be apparent to those skilled in the art, while the IRE in this example (Cesium Iodide) is chemically susceptible to water, and hence subject to degradation during the spectroscopic or radiometric analysis, the protecting wafer is formed from a material (sapphire) which is chemically (and mechanically) resistant to water. Hence, only a thin wafer is necessary to provide sufficient chemical and mechanical resistance for the composite IRE. The composite IRE formed from Cesium Iodide with a thin sapphire wafer is relatively less expensive than if the entire IRE were formed from sapphire. Hence, the overall cost of the composite IRE, and hence the spectroscopic or radiometric instrument, is reduced.

The composite IRE as described herein is designed to be used in spectrophotometers or radiometers known to those skilled in the art. For example, for absorption experiments, the composite IRE structure can be used with a pair of mirrors 22, 23 for directing radiant (IR) energy from a analytical IR radiation source (indicated generally at 26) to a detector or analyzer (indicated generally at 28). Alternatively, or additionally, a pair of light pipes (not shown) can be used for optically linking the composite IRE with the sample compartment of an infrared spectrophotometer, as described in Messerschmidt, U.S. Pat. No. 4,730,882. Another example of a type of spectrophotometer in which the protective wafer of the present invention could be used is disclosed in Sting, U.S. Pat. No. 4,595,833.

In any case, in the composite IRE of the first embodiment, the radiant energy is reflected off mirror 22 and enters the IRE 11 normal to entrance face 30 that is contiguous with bottom surface 13 of IRE 11. The radiant energy reflects off of the first beveled edge 15 to bottom surface 13, and from bottom surface 13 to upper surface 14 of the IRE. The radiant energy passes through upper surface 14 of the IRE and through lower surface 20 of the wafer 12 (with minimal transmission or reflectivity loss) and is incident on the upper (sample) surface 19 of the wafer. The radiant energy undergoes multiple internal reflections off the upper, sample surface of the wafer and the lower surface of the IRE.

After a predetermined number of internal reflections, the energy reflects off second beveled edge 17 and is discharged from the IRE normal to an exit face 32 that is contiguous with bottom side 13 to mirror 23. It is preferred that both first beveled edge 15 and second beveled edge 17 have a reflective coating. A sample (liquid, solid or gas) is placed into contact with upper sample surface 19 of the wafer 12 so that some energy is absorbed by the sample each time the radiant energy reflects from the sample surface 19 to determine the absorption characteristics of the sample.

Referring now to FIG. 2, representing an alternate embodiment or the composite IRE of the invention, a probe 49 includes a probe-shaped composite IRE, indicated generally at 50, is configured to be held within a probe structure P, and includes an IRE 51 configured to have a generally cylindrical body 54 and a generally prism-shaped probe tip 55 with probe structure P sections contoured to house and protect the IRE 51, and a pair of thin wafers 52 and 53 disposed adjacent tip 55, to protect the composite IRE 50 from chemical and mechanical degradation by a sample with which the tip of the probe comes in contact, in the same manner as the previously described embodiment.

The probe-shaped IRE 51 has an upper flat end surface 58 through which beam radiation enters and exits the probe. The probe tip 55 includes first and second beveled edges 59 and 60 which provide angularly disposed optically flat surfaces. IRE 51 can be formed from the same or similar material with the same or similar transmission and refractive index properties as described with reference to IRE 11. IREs with similar properties are also disclosed in Young, U.S. Pat. No. 3,733,130.

Protective wafers 52 and 53 of the composite IRE 50 are located proximate to beveled edges 59 and 60, respectively, and are optically coupled thereto in the same manner as described above (i.e., by mechanical contact or contact with an optically compatible fluid material). The wafers 52 and 53 each have an optically flat surface which is located in close proximity to the optically flat surfaces of the corresponding beveled edges 59 and 60. Wafers 52 and 53 can be formed from the same materials, with the same dimensions, the same chemical and mechanical resistances, and the same transmission and index of refraction properties as described previously.

An incident IR beam 66 from a source of IR analytical radiation (not shown) passes through end surface 58 of IRE 51 and is incident on first beveled edge 59. The beam passes through the first beveled edge 59 and into the first wafer 52 (with minimal transmission or reflectivity losses). The beam is reflected off the outer, sample surface 72 of the first wafer 52 and is directed back through the first beveled edge 59 to the second beveled edge 60.

The beam then passes through the second beveled edge 60 into the second wafer 53 (with minimal transmission or reflectivity losses). The beam is reflected off the outer, sample surface 74 of the second wafer 53 and is directed back through the second beveled edge 60 to the rear surface 58 of the IRE. The exiting radiation beam 76 then passes to a detector or analyzer (not shown) for analysis. Because the wafers are optically coupled to the IRE, minimal transmission or reflectivity losses occur between the wafer/IRE interfaces.

During spectroscopic or radiometric analysis, a sample (liquid, solid or gas) is placed into contact with the outer sample surface of the wafers 52 and 53, through an opening in the tip of probe structure P, so that some energy is absorbed by the sample when the radiant energy is reflected from the outer, sample surfaces of the wafers.

Accordingly, the wafers 52, 53 in the second embodiment protect the IRE 51 from contact with the sample, and hence prevent mechanical or chemical degradation of the IRE. Again, the IRE can be formed from relatively less expensive material to reduce the cost of the composite IRE, and hence reduce the overall cost of the spectroscopic or radiometric instrument.

The principles described above can be applied to other infrared transmitting materials, such as the IREs illustrated in Sting et al., U.S. Pat. No. 5,172,182. One IRE geometry disclosed in this reference has a curved, convex sample contacting surface. According to the principles of the present invention, a thin wafer with a concave inner surface can be optically coupled to the sample contacting surface of the IRE to mechanically and chemically protect the IRE.

Another IRE geometry disclosed in Sting et al. has a fiber optic waveguide which extends from the IRE to the sample. In this case, a wafer can be optically coupled to the end of the fiber optic waveguide to chemically and mechanically protect the fiber optic from degradation by the sample. Accordingly, as should be apparent from the foregoing examples, the principles of the present invention are applicable to a wide variety of commercially-available IREs for spectroscopic and radiometric analysis.

Further, according to additional embodiments of the present invention, the principles of the present invention can be applied to other types of composite ITMs, such as a composite emission cell (FIG. 3) or a composite transmission cell (FIG. 4). In either of these embodiments, at least one wafer is used to chemically and mechanically protect underlying optically transmitting material. Hence, the optically transmitting material of the composite ITM can be formed from a less expensive material which thereby reduces the overall cost of the instrument.

For example, as schematically illustrated in FIG. 3, a composite spectroscopic analysis emission cell, indicated generally at 90, includes an optically transmitting material 100 which directs emitted radiant energy from sample 102 to a remote detector or analyzer (not shown). The sample is contained or bound within a container or crucible 104 and heated by a heater (schematically indicated at 106). Reactive gas can be introduced into the emission cell through opening or port 108. Spectroscopic analysis is performed by detecting the emitted radiant energy from the heated sample. To protect the optically transmitting material 100 from contact with the sample (and/or the reactive gas), wafer 110 is located in optical contact with the inner surface of the optically transmitting material 100 to prevent the sample from contacting the optically transmitting material or the cell atmosphere.

The optically transmitting material 100 in the composite emission cell 90 can be formed from the materials described previously with respect to the IRE in the first embodiment as well as from sodium chloride (NaCl), potassium bromide (KBr), and potassium chloride (KCl), and can have the same transmission and index of refraction properties as described previously.

The protecting wafer of this type of ITM is also formed from the materials described previously and has the same optical transmission and index of refraction properties, chemical and physical resistance, and dimensions as described in the first embodiment. Hence, the wafer protects the optically transmitting material of the composite emission cell and prevents chemical and mechanical degradation thereof.

Figure 4A:
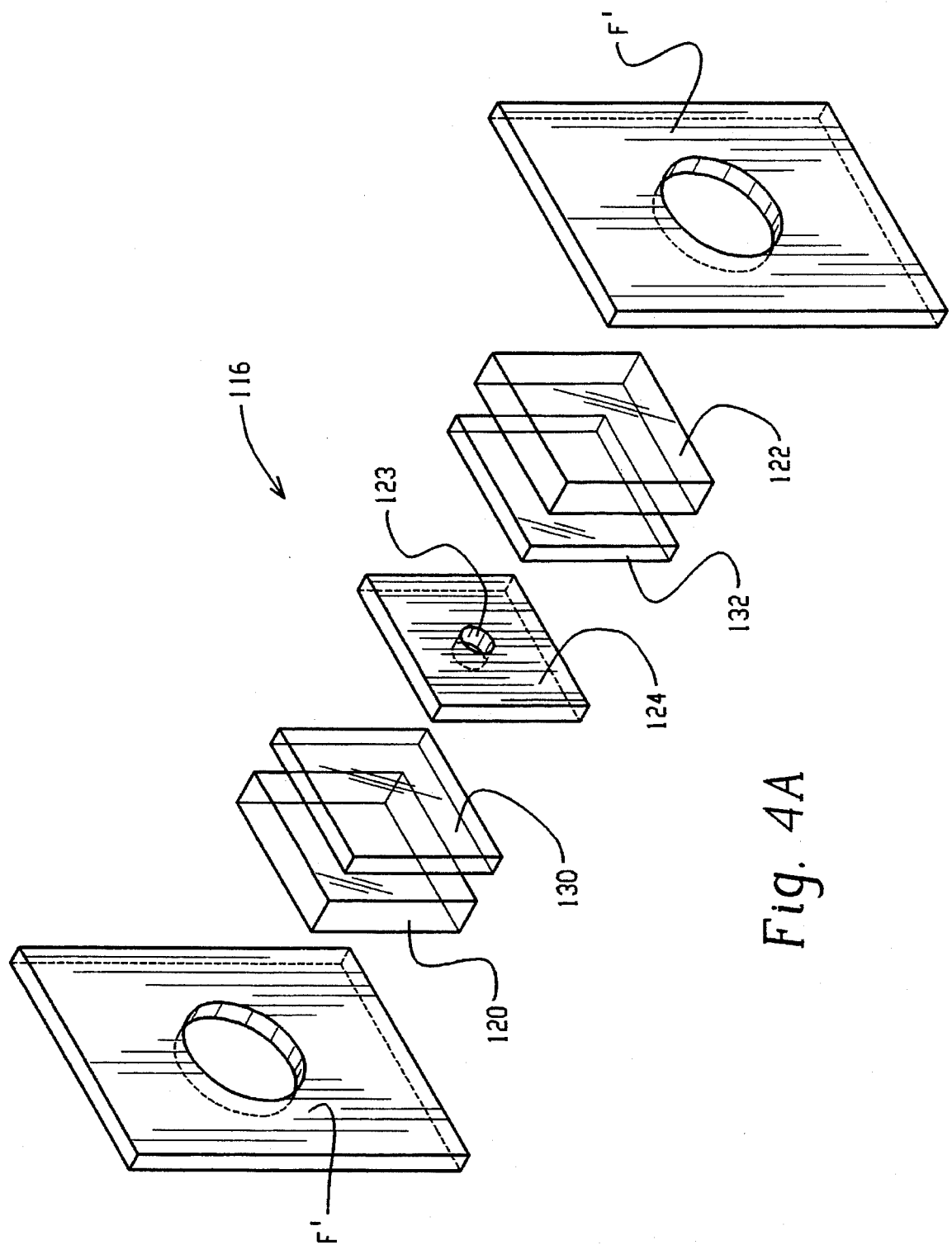
FIG. 4A is an exploded perspective view of an exemplary type of composite transmission cell constructed according to the present invention having an IR transmitting thin sheet or wafer shown in contact with the sample.
Figure 4B:
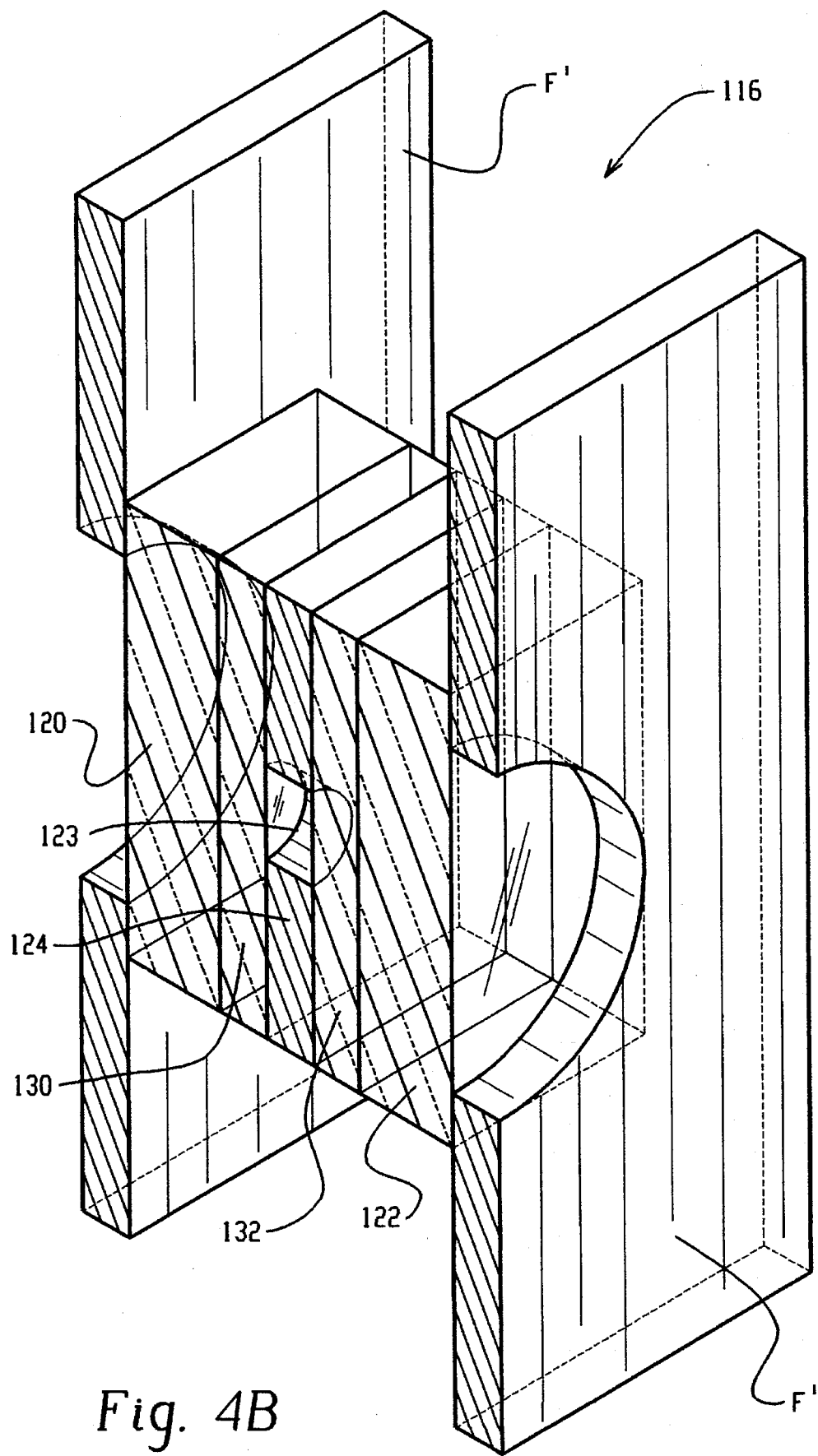
FIG. 4B is a perspective sectional view of the composite transmission cell of FIG. 4A.

Further, as illustrated in FIGS. 4A and 4B, the principles of the present invention can also be applied to a composite transmission cell, indicated generally at 116. The composite transmission cell 116 includes first and second optically transmitting materials 120, 122, held within fixtures F' and spaced a predetermined distance apart from each other. A sample is typically introduced (e.g., contained or bound) in the cavity 123 between the two optically transmitting materials and spectroscopic analysis is performed by directing analytical radiation from a source (not shown) through the first optically transmitting material 120, and through the sample. The radiant energy then passes through the second optically transmitting material 122 and is detected by a detector (not shown). As shown, a sample mask/spacer 124 is also located between the optically transmitting materials 120, 122 to locate (and/or support) the sample. The infrared transmitting materials and mask/spacer can be supported in a fixture as necessary. To protect the optically transmitting materials 120, 122, wafers 130, 132 are located in optical contact with the opposed inner surfaces of the optically transmitting material 120, 122, respectively, to prevent the sample from contacting the optically transmitting materials.

The optical transmitting materials of the composite transmission cell can be formed from the materials described previously with respect to the composite emission cell, and can have the same transmission and index or refraction properties.

The wafers for this type of ITM are also formed from the materials described previously, and have the same optical transmission and index of refraction properties, chemical and physical resistance, and dimensions as described in the first embodiment. Hence, the wafers protect the optically transmitting materials of the composite transmission cell and prevent chemical and mechanical degradation thereof.

As described above, the present invention provides novel and unique composite infrared transmission materials for spectroscopic or radiometric analysis of solid, liquid or gas samples which have broad (or selected) optical transmission ranges, chemical resistivity to the sample, sufficient mechanical strength, and acceptably low cost. The materials reduce the cost of the composite ITMs, and hence reduce the overall cost of the spectroscopic or radiometric instrument.

It will be apparent from the foregoing that changes may be made in the details of construction and configuration without departing from the spirit of the invention as defined in the following claims.

What is claimed is:

1. An apparatus for infrared spectroscopic or radiometric analysis of a sample, comprising:

(i) a fixture for holding first and second optically transmitting materials;

(ii) said first optically transmitting material having bulk optical transmission and index of refraction properties which enable infrared radiation transmission therethrough, said first optically transmitting material being of a type which normally has chemical or mechanical degradation when in contact with a sample during spectroscopic or radiometric analysis;

(iii) said second optically transmitting material held by said fixture relative to said first material to be in optical contact with said first material without being chemically or adhesively bonded to said first material, whereby said second material prevents a sample placed against the second material from contacting the first material during spectroscopic or radiometric analysis of a sample, said second optically transmitting material:

(a) being substantially chemically resistant to a sample, (b) having mechanical properties which prevent significant degradation of the second material when a sample contacts the second material during spectroscopic or radiometric analysis, and (c) having selected optical transmission and index of refraction properties which enable optical transmission from the first material to the second material, or from the second material to the first material, with minimal transmission or reflectivity loss during spectroscopic or radiometric analysis.

2. Apparatus as in claim 1, wherein said second material is in the form of a wafer or thin sheet with a thickness dimension relatively less than a thickness dimension of said first material.

3. Apparatus as in claim 2 wherein the thickness dimension of said second material is in the approximate range of 100 microns to 3 millimeters.

4. Apparatus as in claim 2, wherein said first and second optically transmitting materials have opposing surfaces in optical contact with each other which are optically correct and not more than 2.0 microns apart.

5. Apparatus as in claim 4, wherein said opposing surfaces of said first and second optically transmitting materials are optically flat.

6. Apparatus as in claim 1, wherein said first material is selected from the group consisting of: glass, arsenic-modified selenium glass (SeAs), cadmium sulfide (CdS), cadmium telluride (CdTe), cesium iodide (CsI), germanium (Ge), indium antimonide (InSb), TlBr-TlI, silicon (Si), silver bromide (AgBr), silver chloride (AgCl), sulfur (S), sulfur-selenium glasses ($S_xSe_y$), thallium bromide (TlBr), thallium chloride (TlCl), zinc selenide (ZnSe), zinc sulfide (ZnS), zirconia ($ZrO_2$, cubic), sodium chloride (NaCl), potassium bromide (KBr) and potassium chloride (KCl).

7. Apparatus as in claim 1, further including at least one other optically transmitting material which is a non-adhesive, non-bonding material interposed between said first optically transmitting material and said second optically transmitting material, said at least one other optically transmitting material having refractive index properties compatible with said first and second materials such that minimal transmission and reflectivity losses occur during the spectroscopic or radiometric analysis.

8. Apparatus as in claim 7, wherein said at least one other optically transmitting material is a non-bonding fluid or gel.

9. Apparatus as in claim 1, wherein said second optically transmitting material is selected from the group consisting of: glass, arsenic-modified selenium glass (SeAs), barium titanite (BaTiO$_3$), cadmium sulfide (CdS), cadmium telluride (CdTe), diamond (C), germanium (Ge), indium antimonide (InSb), sapphire (Al$_2$O$_3$), silicon (Si), silver bromide (AgBr), silver chloride (AgCl), strontium titanate (SrTiO$_3$) sulfur (S), thallium bromide (TlBr), thallium chloride (TlCl), titanium dioxide (TiO$_2$), zinc selenide (ZnSe), zinc sulfide (ZnS), and zirconia (ZrO$_2$, cubic).

10. A system for infrared spectroscopic or radiometric analysis of a sample, comprising:

i) a fixture for holding analysis means;
   ii) source means for providing an analytical beam of infrared radiation to the sample;
   iii) detector means for detecting the analytical beam of infrared radiation from the sample;
   iv) analysis means for directing the analytical beam of infrared radiation from said source means to the sample and for directing the analytical beam away from the sample to said detector means, said analysis means including:
      a) a first optically transmitting material held by said fixture having bulk optical transmission and index of refraction properties which enable infrared radiation transmission therethrough, said first optically transmitting material being of a type which normally has chemical or mechanical degradation when in contact with the sample during spectroscopic or radiometric analysis;
      b) a second optically transmitting material held in optical contact with said first material solely by said fixture without any chemical or adhesive bond and located between said first material and said sample to prevent said sample from contacting the first material during spectroscopic or radiometric analysis of the sample, said second optically transmitting material:
   i) being substantially chemically resistant to the sample,
   ii) having mechanical properties which prevent significant degradation of the second material when the sample contacts the second material during spectroscopic or radiometric analysis, and
   iii) having selected optical transmission and index of refraction properties which enable optical transmission from the first material to the second material, or from the second material to the first material, with minimal transmission or reflectivity loss during the spectroscopic or radiometric analysis.

11. A system as in claim 10, wherein said second optically transmitting material is in the form of a wafer or thin sheet having a thickness dimension relatively less than a thickness dimension of said first optically transmitting material.

12. A system as in claim 11, wherein the thickness dimension of said second optically transmitting material is in the range of approximately 100 microns to 3 millimeters.

13. A system as in claim 10, wherein said first optically transmitting material is selected from the group consisting of: glass, arsenic-modified selenium glass (SeAs), cadmium sulfide (CdS), cadmium telluride (CdTe), cesium iodide (CsI), germanium (Ge), indium antimonide (InSb), TlBr-TlI, silicon (Si), silver bromide (AgBr), silver chloride (AgCl), sulfur (S), sulfur-selenium glasses (S$_x$Se$_y$), thallium bromide (TlBr), thallium chloride (TlCl), zinc selenide (ZnSe), zinc sulfide (ZnS), zirconia (ZrO$_2$, cubic), sodium chloride (NaCl), potassium bromide (KBr), and potassium chloride (KCl).

14. A system as in claim 10, wherein said first and second optically transmitting materials have opposing surfaces in optical contact with each other which are optically flat and not more than 2.0 microns apart.

15. A system as in claim 10, further including at least one other optically transmitting material which is a non-adhesive, non-bonding layer of material capable of fluid flow interposed between said first and second optically transmitting materials, said at least one other optically transmitting material further having refractive index properties compatible with said first and second materials such that minimal transmission and reflectivity losses occur during spectroscopic or radiometric analysis.

16. Apparatus as in claim 10, wherein said second optically transmitting material is selected from the group consisting of: glass, arsenic-modified selenium glass (SeAs), barium titanite (BaTiO$_3$), cadmium sulfide (CdS), cadmium telluride (CdTe), diamond (C), germanium (Ge), indium antimonide (InSb), sapphire (Al$_2$O$_3$), silicon (Si), silver bromide (AgBr), silver chloride (AgCl), strontium titanate (SrTiO$_3$), sulfur (S), thallium bromide (TlBr), thallium chloride (TlCl), titanium dioxide (TiO$_2$), zinc selenide (ZnSe), zinc sulfide (ZnS), and zirconia (ZrO$_2$, cubic).

17. A system as in claim 10, wherein said second optically transmitting material is allowed to move relative to said first optically transmitting material within said fixture while remaining in optical contact with said first optically transmitting material.

* * * * *

UNITED STATES PATENT AND TRADEMARK OFFICE
CERTIFICATE OF CORRECTION

PATENT NO. : 5,616,922
DATED : April 1, 1997
INVENTOR(S) : John A. Reffner

It is certified that error appears in the above-identified patent and that said Letters Patent is hereby corrected as shown below:

Column 12,
Line 67, change "fluid" to -- solid --

Signed and Sealed this

Twentieth Day of May, 2003

JAMES E. ROGAN
*Director of the United States Patent and Trademark Office*